United States Patent
Blake et al.

(10) Patent No.: US 6,797,003 B1
(45) Date of Patent: *Sep. 28, 2004

(54) ASPHERIC SOFT LENS

(75) Inventors: Larry W. Blake, Cota de Caza, CA (US); Lee T. Nordan, La Jolla, CA (US)

(73) Assignee: Pharmacia & Upjohn Company, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/161,194

(22) Filed: Dec. 1, 1993

Related U.S. Application Data

(60) Continuation of application No. 08/028,522, filed on Mar. 10, 1993, now abandoned, which is a continuation of application No. 07/626,736, filed on Dec. 13, 1990, now abandoned, which is a continuation-in-part of application No. 07/509,871, filed on Apr. 16, 1990, now Pat. No. 5,019,099, which is a division of application No. 07/262,985, filed on Oct. 26, 1988, now Pat. No. 5,104,590, which is a continuation of application No. 07/232,140, filed on Aug. 15, 1988, now Pat. No. 4,917,681, which is a division of application No. 07/088,227, filed on Aug. 24, 1987, now Pat. No. 4,769,033.

(51) Int. Cl.[7] .................................................. A61F 2/16
(52) U.S. Cl. ...................................... 623/6.23; 623/2.24
(58) Field of Search .......................... 623/6, 6.23, 6.24; 351/160 R, 161

(56) References Cited

U.S. PATENT DOCUMENTS

| 2,823,417 | A |   | 2/1958 | Pasini et al. ................ 425/808 |
| 3,866,249 | A |   | 2/1975 | Flom .............................. 623/6 |
| 3,950,082 | A |   | 4/1976 | Volk ............................ 351/161 |
| 4,010,496 | A | * | 3/1977 | Neefe ............................. 623/6 |
| 4,104,339 | A |   | 8/1978 | Fetz et al. .................. 623/6 X |
| 4,110,848 | A |   | 9/1978 | Jensen ........................... 623/6 |
| 4,179,484 | A |   | 12/1979 | Neefe ......................... 264/2.5 |
| 4,198,714 | A |   | 4/1980 | Jensen ........................... 623/6 |
| 4,208,365 | A | * | 6/1980 | LeFevre ..................... 249/155 |
| 4,373,218 | A |   | 2/1983 | Schachar ....................... 623/6 |

(List continued on next page.)

FOREIGN PATENT DOCUMENTS

| DE | 2556665 | 6/1977 | ..................... 623/6 |
| DE | 2725219 | 12/1978 | ..................... 623/6 |

OTHER PUBLICATIONS

6 Kirk–Othmer, Encyclopedia of Chemical Technology, 724 (3d ed., Wiley–Interscience 1979).*

(List continued on next page.)

*Primary Examiner*—Paul B. Prebilic
(74) *Attorney, Agent, or Firm*—Dinsmore & Shohl LLP

(57) ABSTRACT

An aspheric soft intraocular lens, having an optical power surface, which may have multiple radii portions or aspherical portions, as well as spherical portions, intended to replace the crystalline lens of a patient's eye, in particular after a cataract extraction. Such an aspheric soft lens is molded in a coined mold. A pair of core pins, positioned within the mold cavity during the lens forming process, will produce a pair of haptic-mounting holes within the lens. As the lenses are subsequently tumbled to remove flash, indentations will form adjacent to the haptic-mounting holes. These indentations allow for tangential attachment of the haptic to the lens which, in turn, enables maximum flexibility without exceeding the width of the optic.

1 Claim, 8 Drawing Sheets

U.S. PATENT DOCUMENTS

| | | | | |
|---|---|---|---|---|
| 4,418,991 A | | 12/1983 | Breger | 351/161 |
| 4,449,257 A | * | 5/1984 | Koeniger | 623/6 |
| 4,450,593 A | | 5/1984 | Poler | 623/6 |
| 4,504,982 A | | 3/1985 | Burk | 623/6 |
| 4,512,040 A | | 4/1985 | McClure | 623/6 |
| 4,573,998 A | | 3/1986 | Mazzocco | 623/6 |
| 4,615,702 A | | 10/1986 | Koziol et al. | 623/6 |
| 4,619,662 A | | 10/1986 | Juergens, Jr. | 623/6 |
| 4,640,595 A | | 2/1987 | Volk | 351/160 R |
| 4,659,524 A | | 4/1987 | Neefe | 264/2.5 |
| 4,666,446 A | | 5/1987 | Koziol et al. | 623/6 |
| 4,673,406 A | * | 6/1987 | Schlegel | 623/6 |
| 4,701,288 A | | 10/1987 | Cook et al. | 264/1.4 |
| 4,702,244 A | | 10/1987 | Mazzocco | 623/6 X |
| 4,710,193 A | | 12/1987 | Volk | 623/6 |
| 4,731,078 A | | 3/1988 | Stoy et al. | 623/6 |
| 4,740,282 A | * | 4/1988 | Gesser et al. | 204/165 |
| 4,749,530 A | * | 6/1988 | Kunzler | 264/2.7 |
| 4,753,520 A | | 6/1988 | Silverglate | |
| 4,753,653 A | | 6/1988 | Bissonette et al. | 623/6 |
| 4,759,762 A | | 7/1988 | Grendahl | 623/6 |
| 4,764,169 A | * | 8/1988 | Grendahl | 623/6 |
| 4,769,033 A | | 9/1988 | Nordan | 623/6 |
| 4,836,202 A | * | 6/1989 | Krasner | 606/107 |
| 4,895,585 A | | 1/1990 | Angenent et al. | 425/808 X |
| 4,898,461 A | | 2/1990 | Portney | 351/169 |
| 4,911,714 A | * | 3/1990 | Poley | 623/6.18 |
| 4,917,681 A | | 4/1990 | Nordan | 623/6 |
| 5,066,301 A | * | 11/1991 | Wiley | 623/6.13 |
| 5,104,590 A | * | 4/1992 | Blake | 623/6 |
| 5,236,452 A | * | 8/1993 | Nordan | 623/6 |

OTHER PUBLICATIONS

Peter Hoefer, Translation of German Patent No. 25 56 665, Issued Jun. 30, 1977, pp. 1–9.

Peter Hoefer, Translation of German Patent No. 27 25 219, Issued Dec. 14, 1978, pp. 1–12.

Sean Henahan, "Early Trials Show No Blurring Of Vision With Multifocal IOL," *Ophthalmology Times*, Aug. 15, 1988, p. 27.

Tim Donald, "Silicone Demonstrates Suitable Optic Characteristics In Resolution Testing," *Ocular Surgery News*, vol. 6, No. 16, Aug. 15, 1988, pp. 1, 16–17.

Tom Waters, "Personal Tech 3–D Comes Home," *Discover*, May 1988, pp. 30–32.

Jayne B. Morehouse, "Resolution Efficiency In Water Supported As New IOL Standard," *Ophthalmology Times*, Apr. 15, 1987, pp. 46, 48.

3M Health Care Group, "The 3M Multifocal IOL," *3M HealthCare*, pp. 1–4.

"The Shah Bifocal Universal MK II Intra Ocular Lens."

Norman S. Jaffe et al., "Pseudophakos," published by the C. V. Mosby Company, 1978. Chapter 6, pp. 58–60.

"Ocular Surgery News," Jun. 1, 1987, vol. 5, No. 11, pp. 1, 14 and 15. Article "No Near Corrections Needed By Almost 50 in Bifocal IOL Series."

Ocular Surgery News, Jun. 1, 1987, vol. 5, No. 11, pp. 1, 12 and 13. Article "Bifocal IOL Implanted in England; U.S. Trial May Begin This Month."

* cited by examiner

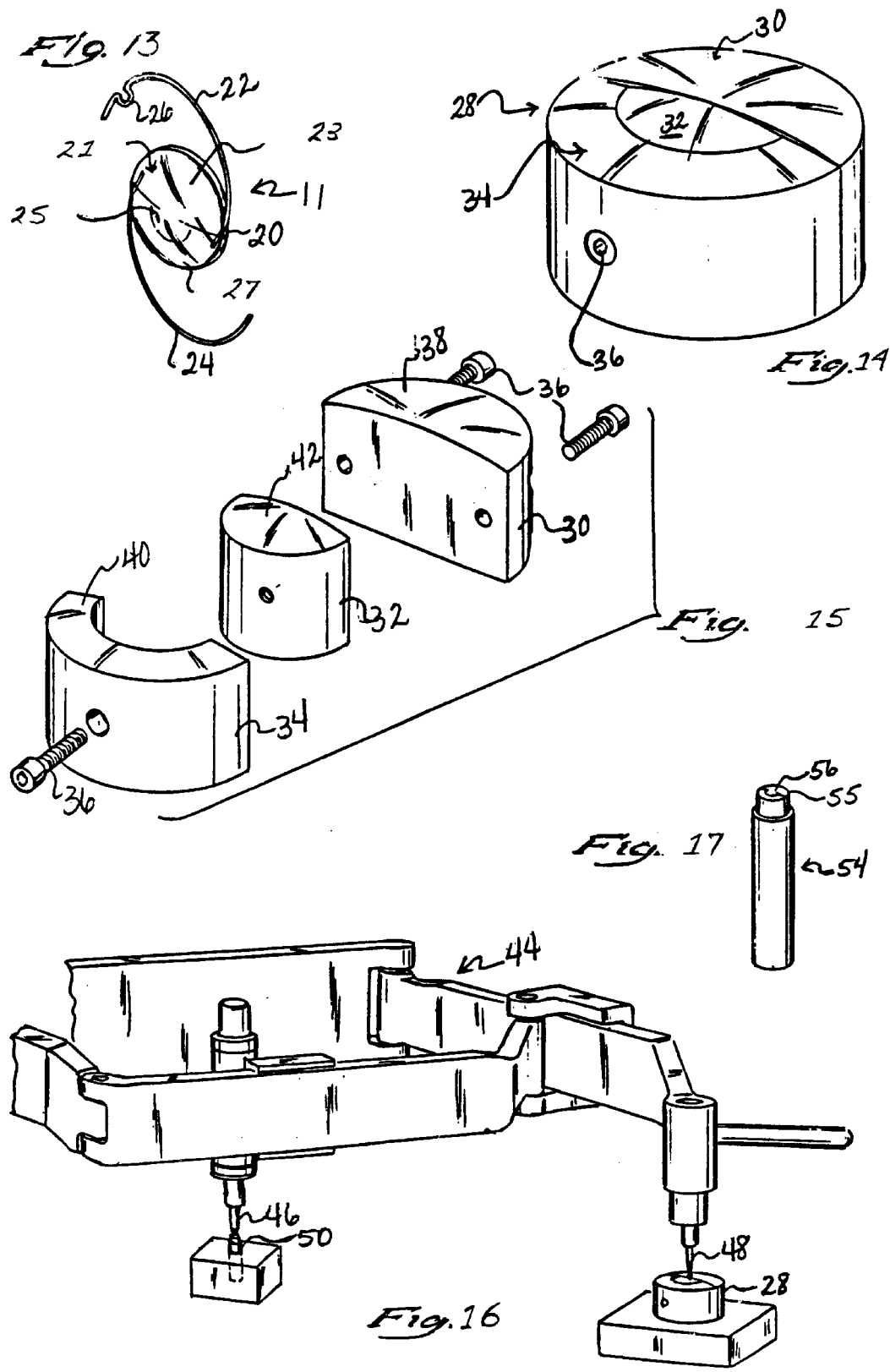

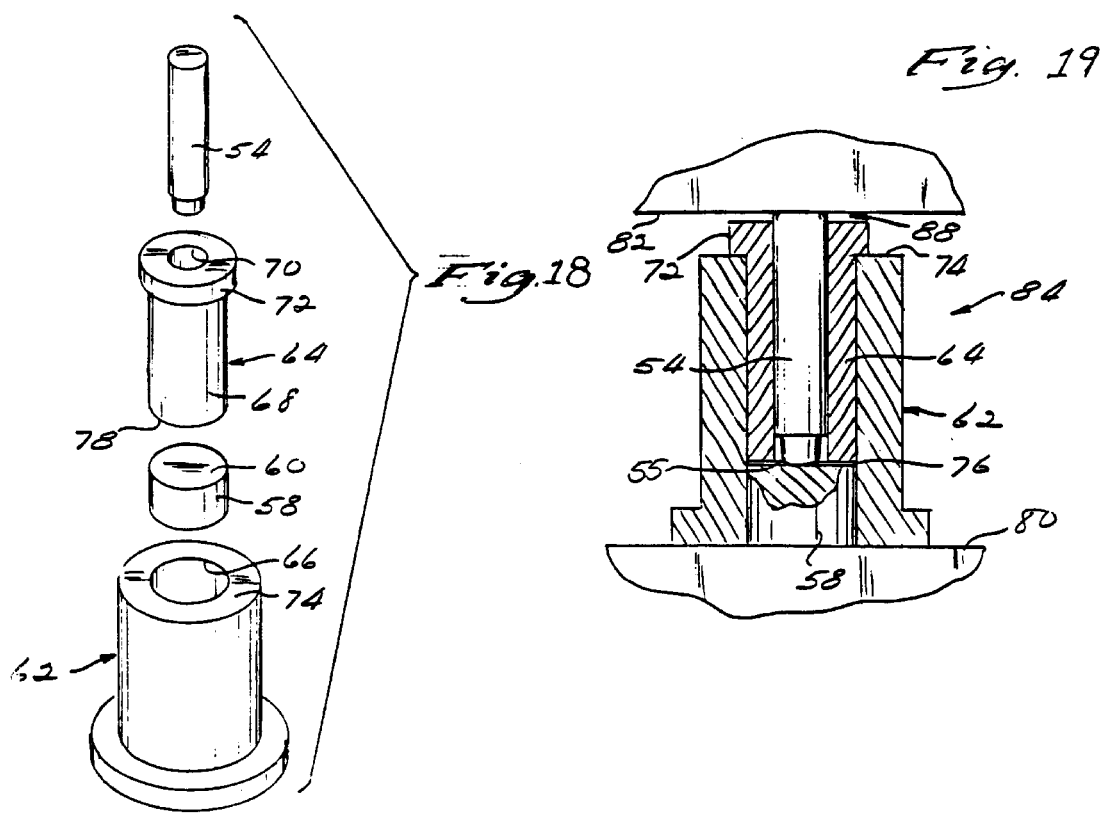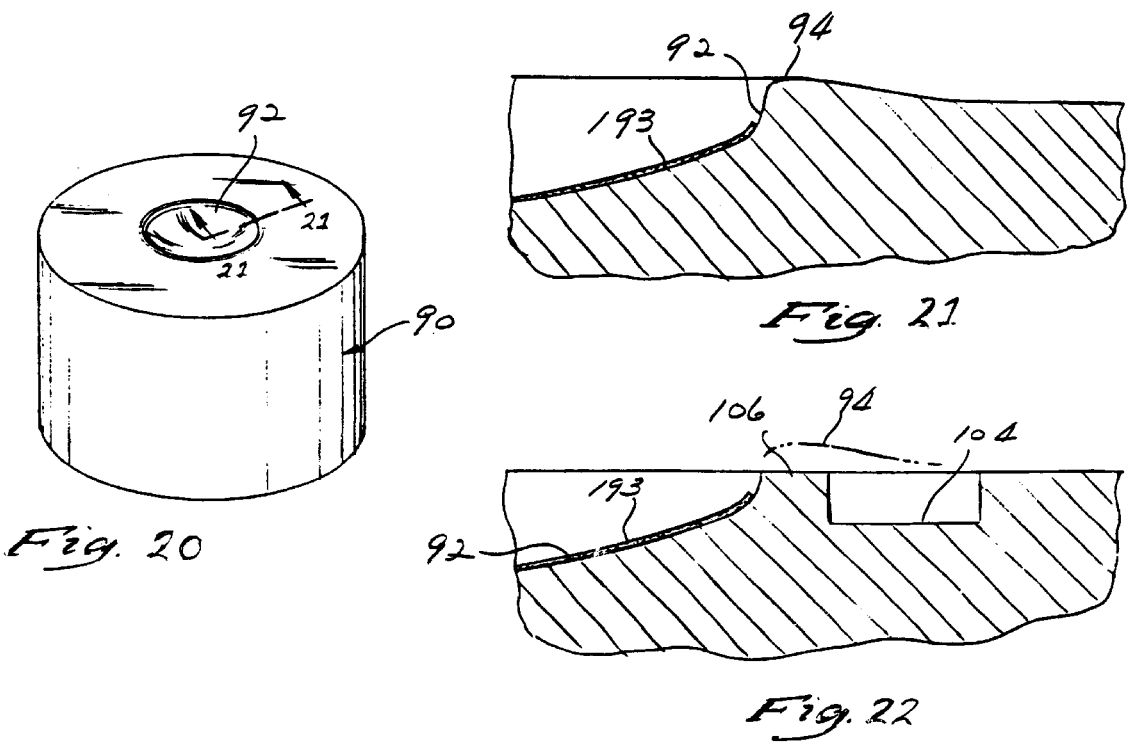

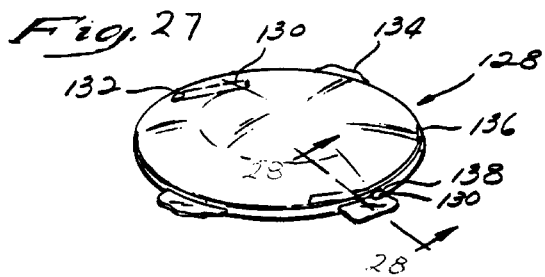
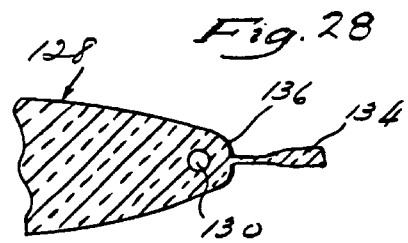
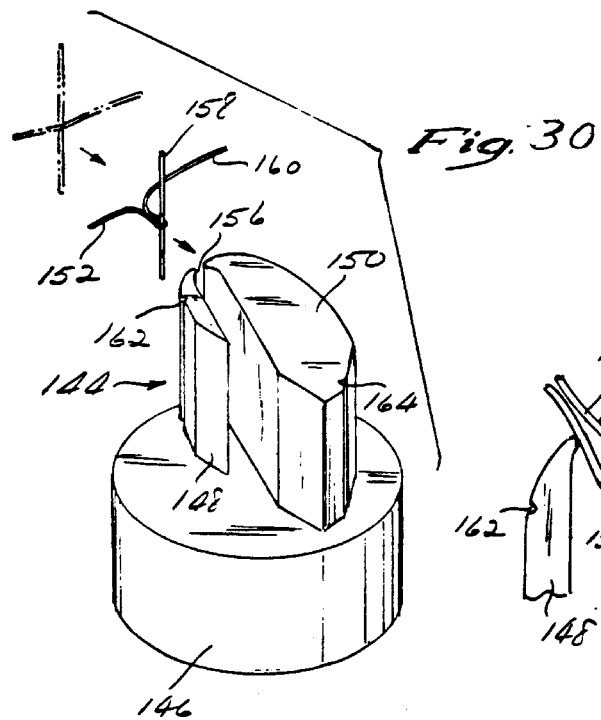
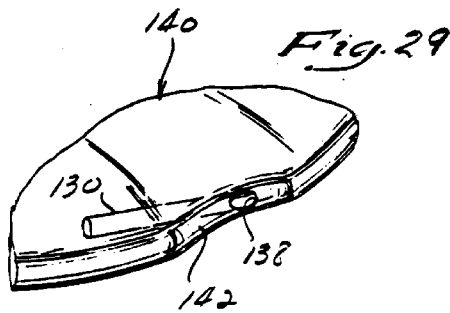
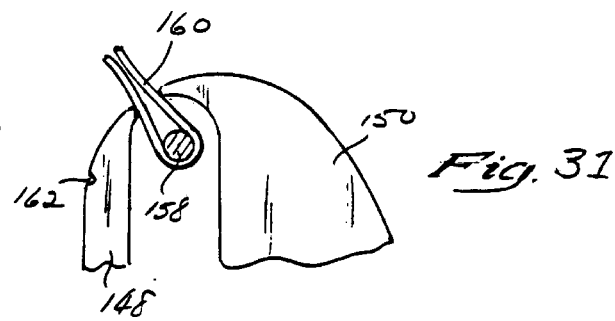
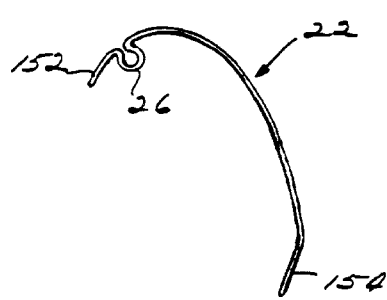
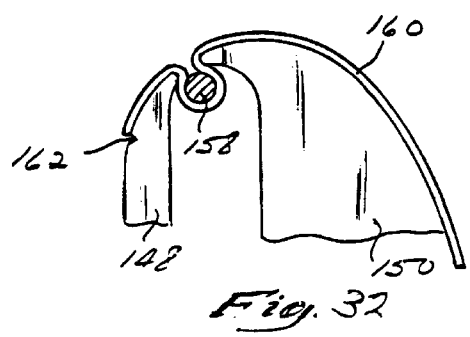

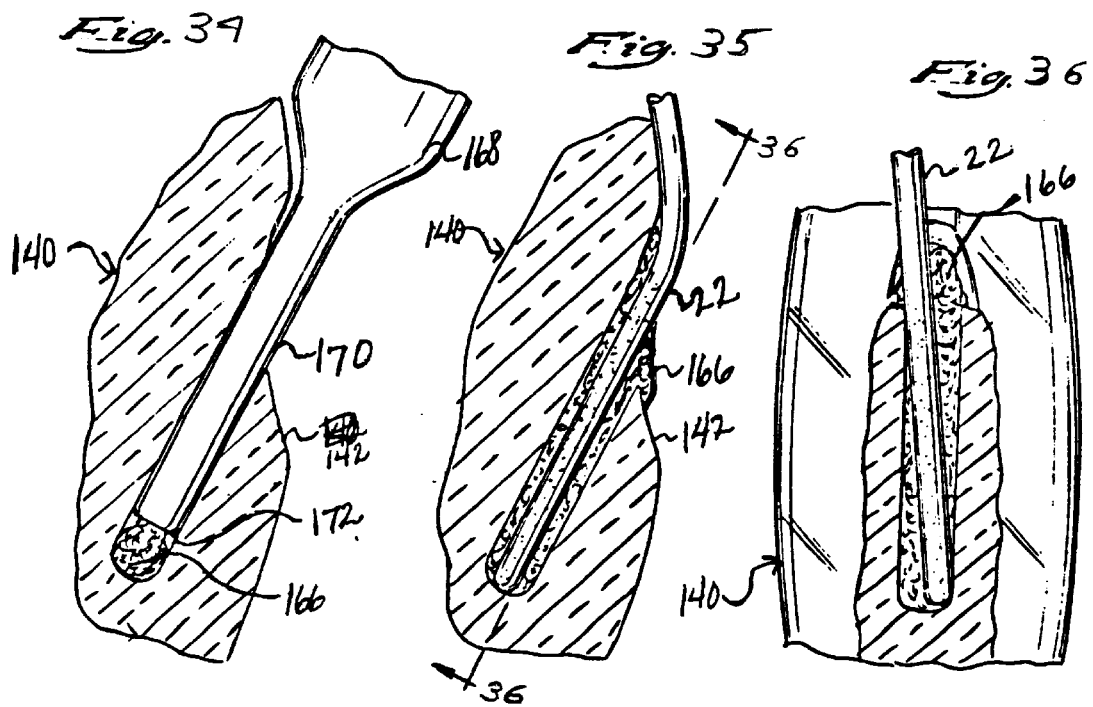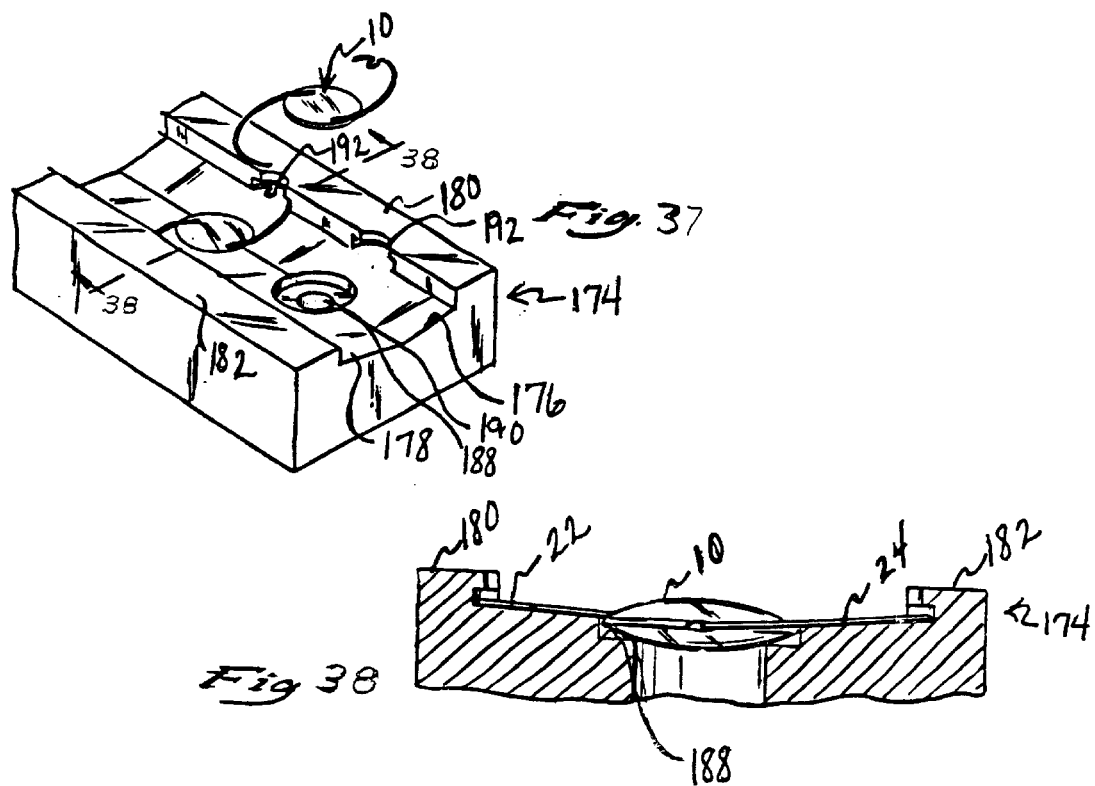

ASPHERIC SOFT LENS

This application is a continuation of Ser. No. 08/028,522 filed Mar. 10, 1993, now abandoned, which is a continuation of Ser. No. 07/626,736 filed Dec. 13, 1990, now abandoned, which is a continuation-in-part of (1) Ser. No. 07/509,871 filed Apr. 16, 1990, now U.S. Pat. No. 5,019,099, which is a continuation of Ser. No. 07/232,140 filed Aug. 15, 1988, now U.S. Pat. No. 4,917,681, which is a division of Ser. No. 07/088,227 filed Aug. 24, 1987, now U.S. Pat. No. 4,769,033, and (2) Ser. No. 07/262,985 filed Oct. 26, 1988, now U.S. Pat. No. 5,104,590.

BACKGROUND OF THE INVENTION

The present invention relates generally to the field of aphakic lenses. More specifically, the present invention relates to an aspheric silicone lens and a technique for fabricating a mold for making such lenses having virtually any surface contour, including non-symmetric surfaces. The invention also includes a technique for attaching and securing support members, or haptics, to such a lens after the lens has been formed and tested.

Intraocular lenses have been increasingly used in the last decade, in particular in aphakic patients after a cataract operation. Intraocular lenses provide many advantages over both spectacle and contact lenses. They permit a better elimination of perceptual problems and reduce image size disparity. Since the intraocular lens is intended to remain in situ, it eradicates the difficulties in inserting and removing contact lenses encountered by elderly patients. The use of an intraocular lens may also be advantageous for those working in unusual environments and for those whose visual requirements for occupation must be fulfilled. Presently, ophthalmologists and eye surgeons recommend that intraocular implant lens surgery be performed when the patient is not likely to manage a contact lens.

According to Norman S. Jaffe et al, *Pseudophakos*, published by The C.V. Mosby Company, 1978, the majority of patients who undergo lens implant surgery in the United States receive implants whose power is estimated from the basic refraction of the eye. Experience has shown however that there are many pitfalls in estimating the basic refraction in this way, in view of the high incidence of residual anisometropia and aniseikonia cases in patients thus corrected. More recently ophthalmologists surgeons have endeavoured to design bifocal intraocular lenses (IOL hereinafter) to focus both the near and far images on the retina. The *Ocular Surgery News*, Jun. 1, 1987, Volume 5, Number 11, reports the latest findings concerning bifocal IOL's. These IOL's, however, provide near and distance vision but do not provide a continuum in the dioptric range. To the best of the inventors' knowledge, there is not known any multifocal intraocular lens.

Intraocular lenses comprise some type of optical element and a support, or haptic, coupled thereto, for properly positioning and centering the intraocular lens within the eye. These lenses have typically included hard polymeric or glass optical elements with metallic or polymeric supports. During the past decade, the medical profession has made widespread use of intraocular lenses comprising polymethylmethacrylate (PMMA), a hard plastic composition. In general, PMMA lenses are cut on a precision lathe, using diamond cutters or injection molded, and then carefully post polished by a critical tumbling process in which the edges of the lenses are radiused and polished.

Recently, workers in the art have utilized lenses comprising a soft, biocompatible material, such as silicone. Silicone lenses have the advantage of being lighter in situ than PMMA lenses, and because they are flexible, they can be folded to reduce their size during implantation into the eye in accordance with conventional surgical procedures. In the implementation of such a procedure, it is the desire of the ophthalmic surgeon to reduce to a minimum the amount of astigmatism and trauma induced in the eye. A technique known as phacoemulsification permits the removal of a diseased or damaged lens and the insertion of a new intraocular lens through an incision of as little as 3 to 4 millimeters. Unfortunately, this procedure is not compatible with the insertion of hard PMMA lenses, and surgeons have found it necessary to increase the length of the incision to at least 8 mm to insert such lenses, obviating at least one advantage of phacoemulsification technology. Methods of producing optical components, such as lenses, have not changed in principle in many years. The main requirements are that the optical surface be polished to a highly accurate shape. In the fabrication of a soft, biocompatible lens, a polished mold, in the shape required for the correct refraction of light for the material selected, is employed. Silicone elastomers, of medical grade, have been found ideally suited for this purpose. The uncured silicone polymer is introduced into the lens cavity of the mold, in an amount dictated by considerations relating to the lens size, refractive power, and structure; and allowed to cure, usually by heating the mold to 250° to 350° F. in a press. Several methods of molding the final lens have been employed and include injection molding, liquid injection molding, compression molding and transfer molding.

It is sometimes desirable to have a lens which includes plural regions having different spherical radii, an aspherical lens, or a lens having aspherical portions. A virtue of such lenses is that the various lens portions yield an increase in dioptric power as the radius of curvature decreases. A problem with making such lenses is the difficulty in obtaining a satisfactory mold of optical quality, having the desired changing radius of curvature. Currently, most molds are made using optical grinding or cutting equipment, or electrical discharge machining (EDM). The mold cavity is then post polished using standard optical lapping techniques. The resultant mold yields a lens having squared-off edges, which cannot be dramatically altered to provide a smooth, radiused edge without substantial risk of damaging the lens. Due to the size of the mold and the difficulties in obtaining an optical finish on a convex surface produced by such a mold, molds for intraocular lenses, having critically measured multiple radii or aspherical portions, using present techniques is very difficult to make and not cost effective. Thus, the present invention offers a method and apparatus for forming molds having such dissimilar shapes.

In another aspect of the present invention, a method of bonding haptics to the periphery of an intraocular lens is described. Haptic materials have included metal loops of various types, however, due to complications related to weight and fixation, such structures have proven undesirable. Presently, polypropylene is a preferred haptic material, although PMMA, nylon, polyamide, polyethylene, polysulfone, and great number of extruded plastics may be used as well. Polypropylene is very resistant to bonding to silicone. It is imperative that the haptics not become detached from the optical element after implantation, as this could have severe repercussions.

The current, preferred method for attaching haptics to the optical element of an intraocular lens is by way of a mechanical lock. This lock may be comprised of an anchor, or loop, through and around which the lens material is cured during the molding process of the lens. One problem associated with such a mechanical bonding technique is that the mechanical anchor often intrudes into the optical zone of the lens, adversely affecting the visual acuity of the patient. Problems also arise when the haptic material is heated to the molding temperature. In general, excessive heat causes the haptic material to become brittle and causes degradation of the material. In addition, the angle that the haptics make with the lens is often critical, ranging from between 0° and 10°. If the optical element is formed through and around the haptics, a separate mold would be required each time it was desired to change the angulation of the haptic. Further, proper angulation of the haptic with respect to the lens is very difficult to achieve during standard molding processes, as the introduction of the lens material into the mold cavity can cause the haptics to be slightly offset. In addition, the haptics tend to get smashed as the two halves of the mold are brought together and closed. Even if the haptic is properly secured to the lens, and able to withstand the molding temperatures and pressures, the lens must be optically tested and approved. A lens rejected for lack of optical quality would obviate the proper positioning and attachment of the haptics thereto. It would therefore be preferable to attach the haptics to the lens after the lens has been formed and optically tested, however, as mentioned above, the bonding of polypropylene to silicone has proven extremely difficult.

Therefore, there is a need in the art for a technique of making intraocular lenses having multiple radii portions or aspherical portions for providing varying degrees of dioptric power. Further, there is a need in the art for a method of attaching haptics to intraocular lenses in general, after the lens has been formed and optically tested.

SUMMARY OF THE INVENTION

It is therefore an object of this invention to provide an intraocular aspheric silicone lens with a full dioptric range and method of making such a lens.

It is also another object of the present invention to produce an intraocular aspheric silicone lens which can be easily and safely implanted in a patient's eye and which can provide optimal postoperative vision.

Another object is to provide an intraocular aspheric silicone lens which can be easily manufactured and can be produced at low cost.

Another object of the present invention is also to furnish an intraocular lens which is more particularly designed for the surgical correction of aphakia following extracapsular cataract extraction.

Briefly, in accordance with the present invention, an intraocular lens has the general shape of a biconvex disk. The proximal side, to be placed against the vitreous humor is substantially spherical, whereas the distal side is composed of three sectors. The upper sector is essentially spherical and extends to the midsection of the disk. The center sector, adjacent the upper sector, extends therefrom to the lower quarter of the disk and is formed of an aspherical sector of decreasing radius of curvature. The lower sector is also essentially spherical. Such a configuration allows light rays impinging on the intraocular lens to be refracted at different angles. The local plane thus varies continuously between a near focal plane for near objects and a far focal plane for distant objects, thereby permitting both near and far vision. The proximal side of the IOL can also be a plane or a concave surface in other embodiments of the present invention.

The present invention provides a technique for fabricating intraocular lenses which may have multiple radii portions or aspherical portions. In a preferred embodiment, such lenses are biconvex lenses and are configured such that the posterior side of the lens is substantially spherical, while the anterior side of the lens is comprised of three sections. The superior half of the anterior side of the lens is spherical, having the same radius of curvature as that of the posterior side. The center of the inferior half of the lens, however, is aspherical, having a precisely defined, steadily decreasing radius of curvature. This aspherical section is met by a second spherical section, having a second radius of curvature, larger than that of the superior half. It would be cost-prohibitive to CNC or EDM to use this configuration to form a mold cavity of optical quality. Accordingly, a reverse mold is created, hardened, and pressed into a softer material, leaving an impression in the softer material which defines the aspherical mold cavity.

This technique begins with the creation of a pattern, machined at ten times the size of the lens on a precision lathe, EDM or CNC machine. A three-dimensional pantograph machine is then employed to transfer the pattern surface to a workpiece one-tenth the size of the pattern. The surface of the workpiece will exhibit a miniature reproduction of the pattern, having the precisely defined surface contours of the pattern on the face thereof and will be used as a coining mandrel. The coining mandrel is then hardened and painstakingly polished to produce an optical surface, while maintaining the surface contours replicated from the surface of the pattern. A blank, which will form a mold half, is optically lapped to produce a flat optical surface. The polished coining mandrel is then pressed into the blank under tremendous pressure to impress upon the blank the desired mold cavity configuration. It is important that the contacting faces of both the coining mandrel and the blank be polished to optical surfaces, as imperfections in either of these pieces will inevitably manifest itself on the resultant lens.

In another aspect of the present invention, a method of tangentially bonding haptics to the lens is described. In this method, core pins are inset into the mold on diametrically opposed sides prior to the introduction of the lens material. No mold release agents are necessary, as the lens material does not adhere to the mold surfaces. The lens material forms and cures around the core pins, but does not bond to them, while the lens is being molded. The core pins are then removed, leaving behind small apertures adjacent the edge of the lens. While the lens is being tumbled and polished, the area of the lens adjacent these apertures abrades more rapidly than the remaining perimeter of the lens, producing indentations. The indentations enable tangential attachment of the haptics to the lens.

Adhesive bonding of the haptics, which are preferably formed of polypropylene, PMMA, polyester or other biocompatible materials, to silicone lenses is accomplished by improving the adhesive properties of the polypropylene through surface treatment of the haptic with a high frequency corona discharge and a silicone primer. The surface-treated haptics are then bonded within the apertures adjacent the lens edge with a translucent, non-flowing, soft silicone adhesive. Adhesive bonding of the haptic to the lens is preferable in that it permits flexibility in the angulation of the haptic with respect to the lens. In addition, subsequent attachment of the haptics to the lens obviates the problems associated with forming the lens with the haptics intact, such as the tendency of the haptics to become brittle due to the curing temperatures and the need to machine separate molds for various angular arrangements. Further, subsequent haptic attachment advantageously provides much flexibility in the choice and use of various haptic materials having varying diameters and configurations. Moreover, the optical element may be optically tested and measured prior to the attachment of the haptic to the lens. In yet another aspect of the invention, a method of calculating dioptric power at any point on the varifocal portion of a nonspherical lens is discussed.

These, as well as other features of the invention will become apparent from the detailed description which follows, considered together with the appended drawings.

BRIEF DESCRIPTION OF THE DRAWING

Other objects and advantages of this invention will become more apparent from the following specification taken in conjunction with the drawing wherein:

FIG. 13 is a perspective view of an intraocular lens, made by the techniques described herein;

FIG. 14 is a perspective view of a reverse mold pattern, ten times the size of the final reverse mold, having an aspherical portion;

FIG. 15 is an exploded perspective view of the pattern illustrated in FIG. 14, showing the various sections of the pattern;

FIG. 16 is a perspective view of a pantograph, used to replicate the pattern onto the surface of a coining mandrel, one-tenth of the original size;

FIG. 17 is a perspective view of a reverse mold, or coining mandrel, having an optical surface polished thereon;

FIG. 18 is an exploded perspective view of a mold forming assembly, used in the fabrication technique of the present invention;

FIG. 19 is a cross-sectional view of the forming assembly of FIG. 18, just prior to pressing the mold cavity;

FIG. 20 is a perspective view of a mold half formed in the assembly of FIG. 19;

FIG. 21 is an enlarged cross-sectional view, taken along line 21—21 of FIG. 20, showing the slight eruption of metal displaced during the mold forming process;

FIG. 22 is an enlarged partial cross-sectional view of the mold half of FIG. 23, showing the ground-off eruption in phantom lines and an overflow groove which has been machined around the optical cavity;

FIG. 27 is a perspective view of a newly molded lens, showing the flashing, sporadically disposed about the periphery of the lens;

FIG. 28 is a cross-sectional view, taken along line 28—28 of FIG. 27;

FIG. 29 is a perspective view of an edge of the lens adjacent the aperture formed by the core pin subsequent to the tumbling of the lens;

FIG. 30 is a partially exploded perspective view of a forming mandrel used for making a control haptic;

FIG. 31 is a top plan view of the forming mandrel illustrated in FIG. 30;

FIG. 32 is top plan view of the forming mandrel illustrated in FIGS. 30 and 31, showing the control haptic being formed;

FIG. 33 is a plan view of a control haptic;

FIG. 34 is a partial cross-sectional view of an edge of a lens, illustrating the aperture being filled with adhesive;

FIG. 35 is a partial cross-sectional view of an edge of a lens, showing the bonding of a haptic into the hole;

FIG. 36 is a cross-sectional view, taken along line 36—36 of FIG. 35, showing the angulation of the haptic within the hole;

FIG. 37 is a perspective view of a dihedral holding fixture used to maintain the haptics at a predetermined angle within the lens while the adhesive cures;

FIG. 38 is a cross-sectional view, taken along line 38—38 of FIG. 37, showing the disposition of a lens within the dihedral holding fixture;

DESCRIPTION OF THE PREFERRED EMBODIMENT OF THE INVENTION

Figure 1:
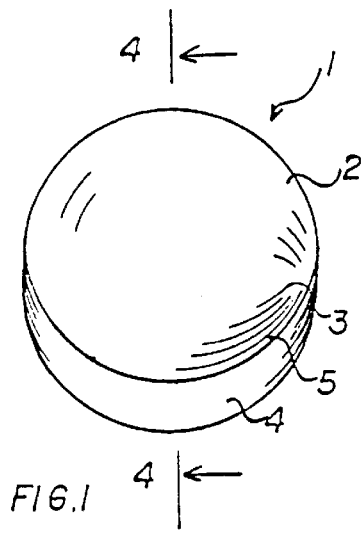
FIG. 1 is a front perspective view from the distal side of an intraocular lens common to the first, second and third preferred embodiments of the invention.

Referring now to FIG. 1, there is represented a front perspective view from the distal side (or external side) of the intraocular lens of the present invention. The IOL of the present invention is particularly designed for the surgical correction of aphakia following extracapsular cataract extraction. This lenticulas is to be implanted in the posterior chamber of the patient's eye and is designed to be placed in the ciliary sulcus.

As illustrated in FIG. 1, the IOL of the present invention has the general shape of a biconvex disk. The distal side 1, represented in FIG. 1, has a generally spherical form with the exception of a sector 3 extending approximately from the mid-section of the distal side 1 to the lower quarter 4. The aspherical sector 3 is configured such that the radius of curvature decreases monotonously from the value $R_1$ of the radius of the upper spherical sector 2, to a lower value $R_0$. The lower spherical sector 4 has the same radius as the upper spherical sector 3, namely $R_0$. Because $R_0$ and $R_1$ are different, the aspherical sector 3 and the lower spherical sector 4 form an obtuse angle. $R_0$ varies typically between 7 mm and 9 mm, whereas $R_1$ varies between 8 mm and 10 mm radius of curvature in the preferred embodiments of the present invention. The discontinuity 5 between the aspherical sector 3 and the lower spherical quarter 4 is blocked out by dark or etched plastic in order to eliminate glare. However, the transition may be so slight as to preclude the need for any blocking or etching. The IOL is preferably made of polymethylmethacrylate (PMMA) or any other suitable material for IOL's such as silicon or hydrogel. The asphericity of the sector 3 not only occurs along the axis X of the intraocular lens, hereinafter referred as the vertical axis, but also along the axis Z of the lens, hereinafter referred as the horizontal axis. More particularly, the planes XY, XZ and YZ are respectively called hereinafter the vertical plane, the distal plane and the horizontal plane of the lens. The discontinuity 5 therefore extends from the lower quarter 4 to the mid-section of the lens on the edges and has an annular shape, as shown in FIG. 1.

Figure 2:
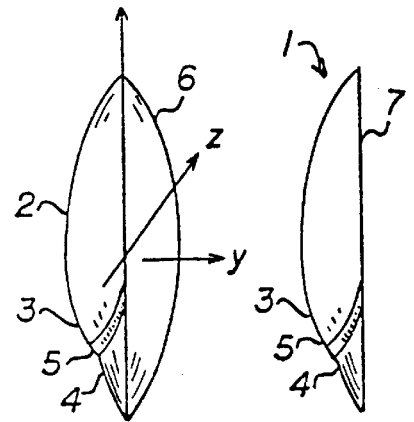
FIG. 2 is a side view of a first preferred embodiment of the present invention.

Now turning to FIG. 2, there is illustrated the first embodiment of the present invention in a side view. The proximal side 6 is a convex surface in this embodiment. As illustrated in FIG. 1, the distal side 1 shows the three sectors hereabove described, namely the upper spherical sector 2, the central aspherical sector 3 and the lower spherical quarter 4.

Figure 3:
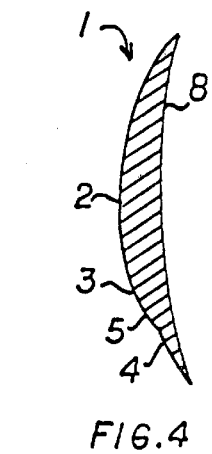
FIG. 3 is a side view of a second preferred embodiment of the present invention.
Figure 4:
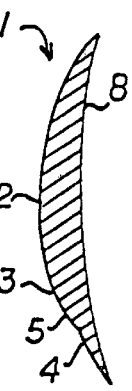
FIG. 4 is a cross-sectional view of a third preferred embodiment of the present invention taken along line 4—4 of FIG. 1.

In FIGS. 3 and 4, there are illustrated two other embodiments of the present invention. In FIG. 3, the proximal side 7 is a plane, whereas in FIG. 4, the proximal side 8 is a concave surface. In each of the aforementioned embodiments, the distal side has the same configuration.

Figure 5:
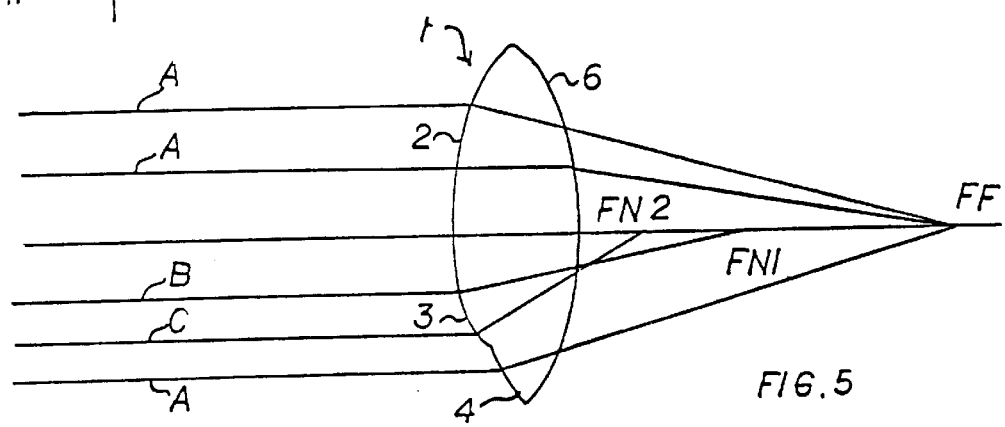
FIG. 5 is an optical diagram illustrative of the variable multifocal effect achieved by the first preferred embodiment of the present invention.

FIG. 5 is an explanatory optical diagram illustrating the multifocal property of the first preferred embodiment of the present invention as described hereabove. It should be noted, however, that the optical diagram of FIG. 5 holds true for the other embodiments of the present invention. A ray of light A impinging upon the lens on its spherical sector 2 is focused in the far focal plane, as indicated by FF. The aspherical sector is tangentially adjacent to the spherical sector 2 about the center of the mid-section of the IOL. As mentioned hereabove, the radius of curvature of the aspherical sector 3 varies from $R_0$, value of the radius of the spherical sector 2, to $R_1$. A ray of light C impinging upon the bottom of the aspherical sector is thus focused in a plane FN2 located between the lens and the far focal plane by virtue of elementary optical laws. The optic of the IOL of the present invention provides therefore both near vision through the aspherical sector 3 and distance vision through the spherical sectors 2 and 4. Light B from intermediate objects is also adequately focused in FN1 by the aspherical sector 3 because of its varying radius of curvature. The degree of sphericity can be chosen to permit a full dioptric range, thereby providing optimal post-operative vision. The principle underlying the functioning of the multifocal IOL herein disclosed, reposes on the general concept that the brain selects one or the other of the images focused on the retina by the IOL. This selection is based on differences in contrast between the images perceived by the brain. Through each of the sectors of the IOL, the focused image and the unfocussed images are projected onto the retina, and the brain immediately selects the focused image. A loss of contrast is noticeable but not significant.

Figure 6:
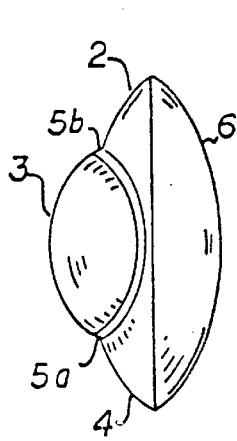
FIG. 6 is a side view of the fourth embodiment wherein the aspherical sector extends over the entire central part of the lens.

Now turning to FIG. 6, there is represented a side view of a fourth embodiment of the present invention wherein the aspherical sector 3 extends approximately from the lower quarter 4 to the upper quarter 2. This aspherical sector 3 therefore defines two discontinuities 5a and 5b which can be both blocked out to eliminate glare as stated hereinbefore.

Figure 7:
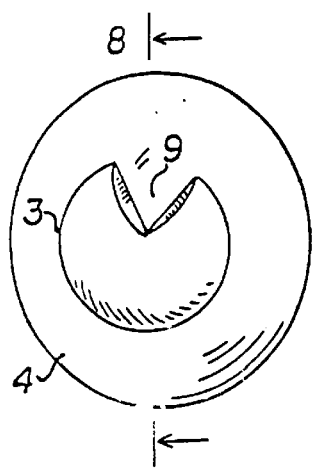
FIG. 7 is a perspective view of the fifth embodiment which includes an upper spherical angular sector.
Figure 8:
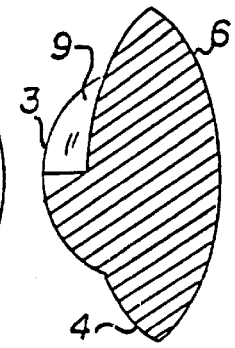
FIG. 8 is a cross-sectional view thereof taken along line 8—8 of FIG. 7.

In the fifth embodiment illustrated in FIGS. 7 and 8, the aspherical sector 3 extends over the entirety of the central part of the intraocular lens as in FIG. 6 with the exception of an angular sector 9 in the upper part of the lens. More generally, the aspherical sector 9 can take various shapes. The number of degrees of the aspherical sector in the plane of the lenticulas can vary from 180 degrees to 360 degrees as in FIG. 6 and can take any intermediary value, as illustrated in FIG. 7. A value inferior to 180 degrees is not excluded but may impair the near vision properties of the intraocular lens.

Figure 9:
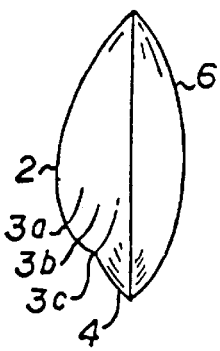
FIG. 9 is a side view of the sixth embodiment wherein the asphericity of the aspherical sector is achieved in discrete steps.

Referring to FIG. 9, there is illustrated a sixth embodiment of the present invention similar to the first embodiment, but wherein the asphericity of the sector 3 is achieved in discrete steps. The aspherical sector extends from the lower quarter 4 to the mid-section 2 as in FIG. 2. However, the aspherical sector is constituted of three spherical domains 3a, 3b and 3c, of decreasing value from $R_0$ to $R_1$. It should be understood that a greater number of discrete steps can be envisaged. In the example illustrated in FIG. 9, the spherical sectors 3a, 3b and 3c, have respectively the following refractive powers: 1 diopter, 2 diopters and 3 diopters. Such an arrangement allows to obtain a continuum of refractive powers. Because the asphericity of the sector 3 extends both horizontally and vertically, the spherical sectors 3a, 3b and 3c take the form of concentric crescents around the center of the intraocular lens in the distal plane thereof.

Figure 10:
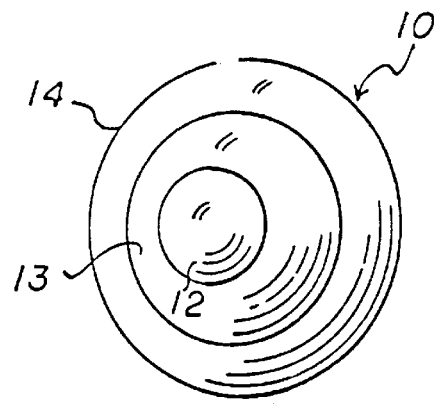
FIG. 10 is a perspective view of the seventh embodiment using concentric spherical and aspherical sectors.
Figure 11:
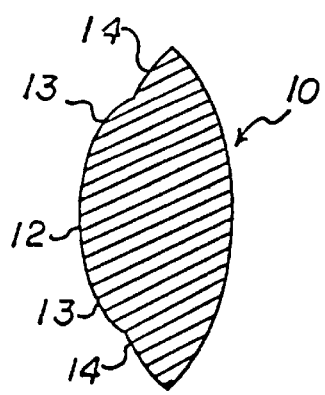
FIG. 11 is a median cross-sectional view thereof.
Figure 12:
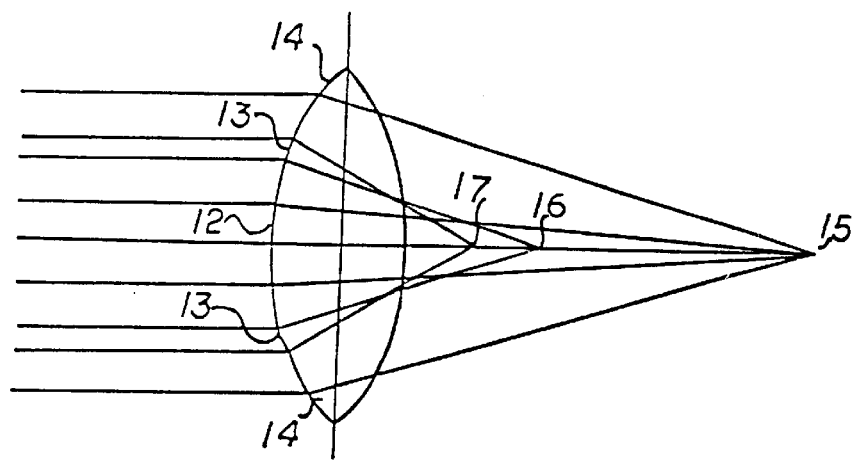
FIG. 12 is an optical diagram illustrative of the various multifocal effects obtained with the seventh embodiment of the invention.
Figure 23:
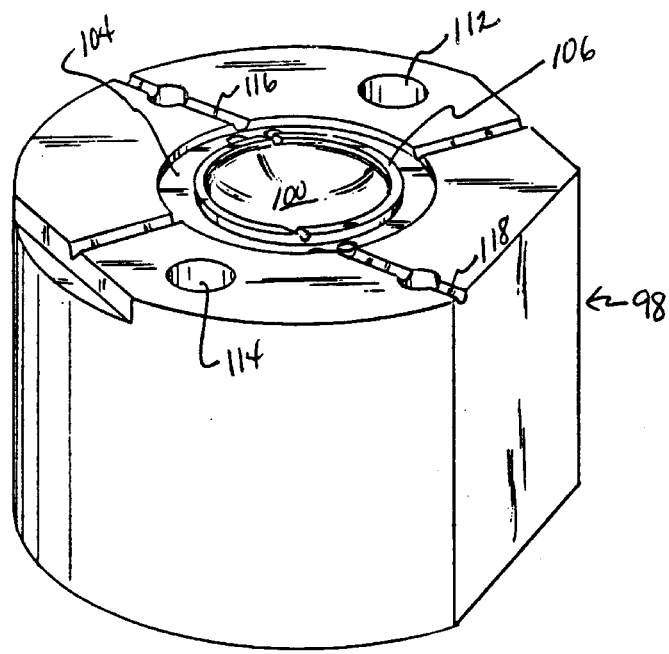
FIG. 23 is a perspective view of a top half of a mold made in accordance with the technique of the present invention.

FIGS. 10 through 11 illustrate a seventh embodiment of the invention using concentric spheric and aspheric zones. More specifically, the intermediary sector 13 is aspherical, while the central sector 12 and peripheral sector 14 are spherical. As in the previously described embodiments, the radius of curvature of the aspherical sector 13 decreases progressively as we get close to the peripheral sector 14. This embodiment of the invention is symmetrical about all meridians. As the diagram of FIG. 12 indicates, the most distant focal point 15 corresponds to the spherical median and peripheral sectors 12 and 14, while the various proximal focal points 16, 17 correspond to the continuously variable aspherical sector 13.

It should be observed that minor variations of the aforedescribed IOL are envisageable, such as displacing upwards or downwards the three convex sectors hereabove described. In particular, the aspheric sector can begin anywhere on the surface of the intraocular lens and can be of any radius. In the embodiments hereinbefore described, the aspherical sector has the same radius as the lens itself and therefore extends from one edge of the lens to the other edge. A configuration wherein the aspherical sector occupies only the central part of the lens, is possible and would serve the same purpose as the embodiment more fully described hereabove. It should also be noted that the proximal side can be otherwise configured.

The technique of forming such an intraocular aspheric silicone lens is now described with reference to FIGS. 13 through 41. There is shown generally at 11 in FIG. 13, an intraocular lens formed using the techniques of the present invention. Preferably, the intraocular lens 11 is a biconvex lens having a first, or anterior side 21 and a second, or posterior side (not shown). The posterior side will reside in the capsule of the eye adjacent the vitreous humor, and is substantially spherical. The anterior side 21, however, as schematically illustrated, is asymmetric, and is formed of three sections 23, 25, 27. The upper, or superior section 23 occupies the upper half of the lens and is substantially spherical, having essentially the same radius curvature as that of the posterior side of the lens. The center section 25 adjacent the superior section 23, extends from the center of the lens to the lower quarter, and exhibits an aspherical surface, having a gradually decreasing radius of curvature. The third section 27 of the lens 10 is also spherical, but exhibits a longer radius of curvature than that of the superior section 23 so as to provide a flatter surface and thus greater strength and thickness near the edge 20 of the lens, at the juncture of the two spherical sections 23, 27. A pair of support members, or haptics 22, 24 are secured to the lens 10 on diametrically opposed sides, and aid in centering the lens 10 within the eye after implantation. The superior, or control haptic 22 is provided with a horseshoe-like kink 26 which enables the ophthalmic surgeon to readily determine which is the superior portion 14 of the lens 10 and permits manipulation of the lens 10 during surgery.

A pattern 28, or reverse mold of the desired surface of the anterior side 21 of the lens 10, preferably made out of aluminum with a CNC machine and scaled ten times larger than the desired size, is illustrated in FIGS. 14 and 15. As most clearly illustrated in FIG. 15, the pattern 28 comprises three major components: a large semi-circular block 30, a small semi-circular block 32, and an arcuate block 34, having an outer diameter corresponding to the diameter of the large semi-circular block 30, and an inner diameter corresponding to the diameter of the small semi-circular block 32. The blocks 30, 32, 34, are secured together by a plurality of bolts 36. The larger semi-circular block 30 has a spherical surface 38, and corresponds to that portion which will ultimately be the superior half 23 of the anterior side 21 of the lens 10. Likewise, the arcuate block 34 corresponds to the outer, inferior section 27 of the lens 10, and is also provided with a spherical surface 40, although somewhat flatter than that of the large semi-circular block.

It is noteworthy that when making the pattern, the radius of curvature of the various portions must be shorter than that of the desired surface of the mold cavity to allow for "spring back" of the coined surface. Specifically, it has been found that the center of the mold cavity, which is deeper than the periphery, "springs back" more than the periphery, since it has yielded more than the periphery. Empirical data has shown that for a stainless steel mold cavity, the coined mold will have a radius of curvature which is 1 to 2% larger than the radius of curvature of the coining mandrel. A correction factor for this difference is made in the pattern by reducing its radii of curvature by 1 to 2%. In addition, silicone lenses made in such a mold tend to shrink a uniform 3.7% during the lens forming process. Therefore, the pattern, in addition to having shorter radii of curvature, should be enlarged by a factor of 3.7% to allow for such shrinkage.

The radius of curvature of an optical element is proportional to the focal length of that element. As the radius of curvature of an optical element decreases, the dioptric power, which is defined as the inverse of the focal length when measured in meters, increases. The small semi-circular block 32 is configured such that the radius of curvature, on the surface 42 thereof, steadily decreases from a first value, $R_0$, equal to the radius of curvature of the large semi-circular block 30, to a lower value, $R_N$, determined by the desired change in the base power of the varifocal, or aspherical portion 25 of the lens 10.

Figure 41:
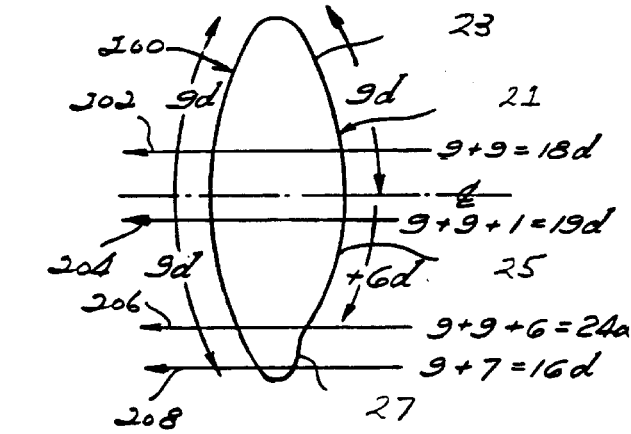
FIG. 41 is a profile of an intraocular lens, schematically illustrating the dioptric power increase of light passing through various portions of the lens, having various radii of curvature.
Figure 40:
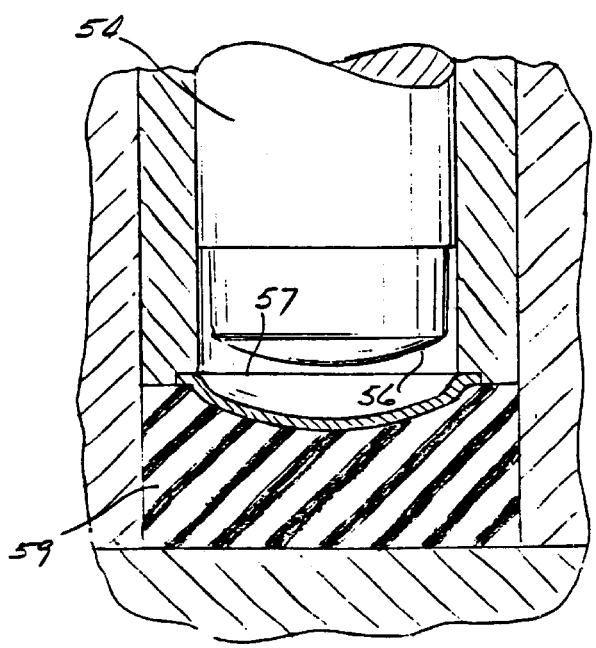
FIG. 40 is a partial cross-sectional view of an alternative coining assembly.

In a biconvex lens, as shown in FIG. 13, and schematically illustrated in FIG. 41, the entire posterior side 200 and the superior half 23 of the anterior side 21 of the lens are of fixed curvatures which determine the base power of the lens after implantation in the eye. The inferior half of the anterior side 21, is capable of providing varying levels of accommodation by virtue of the aspherical portion 25 of the lens. As noted above, the dioptric power of an intraocular lens is typically controlled by varying the anterior and/or posterior radii of the optical element. If, for example, as illustrated in FIG. 41, the posterior side 200 is of a fixed radius of curvature, corresponding to a dioptric power of 9 diopters, and the superior half 23 of the anterior side 21 exhibits the same radius, and thus the same power of 9 diopters, then light impinging on the lens in this area, as designated by line 202, would be focused with a dioptric power of 18 (9+9) diopters. As the center section 25 of the anterior side 21 under goes a change in its radius of curvature, the focal point of light impinging therethrough would also change. If, for example, the intraocular lens were designed to provide a steadily increasing power of 6 diopters, light impinging on the lens ⅙ of the way down the aspherical section, as designated by line 204, would be focused with a power of 19 diopters (9+9+1), whereas light impinging on the lens at the bottom of the aspherical portion (line 206) would be focused with a power of 24 diopters (9+9+6). Finally, light impinging on the inferior portion of the lens, corresponding to the flatter spherical section of the lens 27, and designated by line 208, would have a power of 16 diopters (9+7). This effect was demonstrated in theory by Lee T. Nordan in U.S. Pat. No. 4,769,033, entitled "Intraocular Multifocal Lens," issued on Sep. 6, 1988, a continuation-in-part of U.S. patent application Ser. No. 069,197, filed on Jul. 2, 1987, now abandoned.

Figure 39:
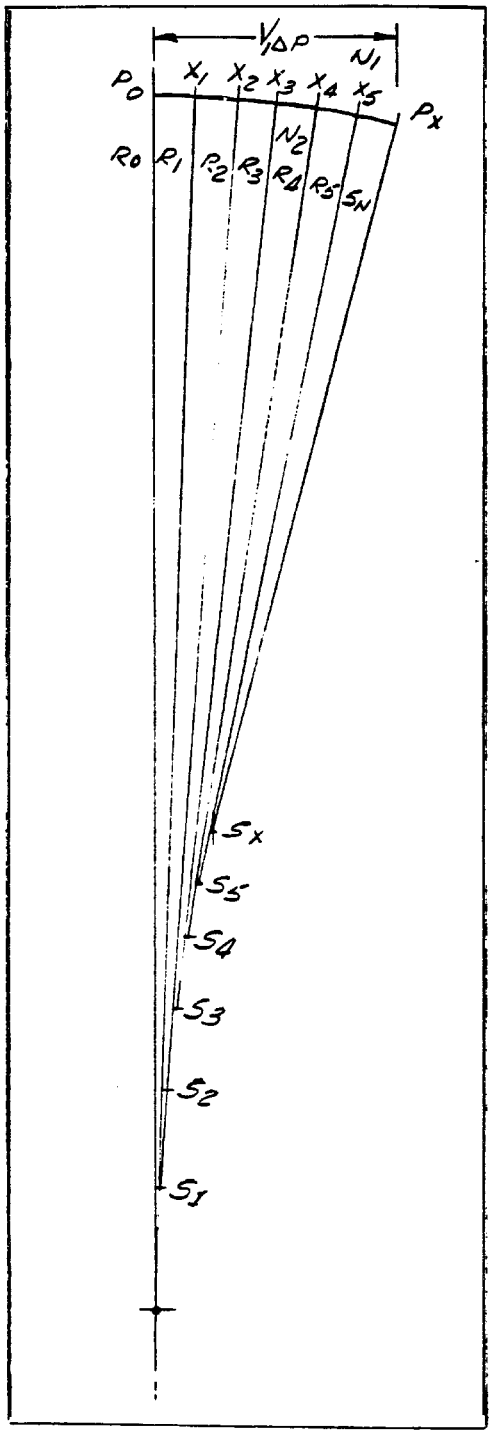
FIG. 39 is a graph plotting the radius of curvature of the aspherical portion of the lens.

FIG. 39 schematically illustrates the changing radius of curvature ($R_0 \ldots R_N$) throughout the varifocal portion of the lens. The radius of curvature ($R_0$) begins at the same radius as that of the spherical portion, and then gradually decreases. The radius of curvature ($R_x$) of the varifocal or aspherical portion of the lens, can be determined at any point by the equation:

$$R_x = \frac{R_0}{1 + KX}$$

where:

$$K = \frac{R_0 P}{V(N_2 - N_1)}$$

and where:
P=the total change in power from $R_0$ to $R_N$;
V=the width of the varifocal portion of the lens;
$N_2$=the index of refraction of the lens; and
$N_1$=the index of refraction of aqueous in situ.
Thus, the aspherical portion of the lens is a solid of rotation, formed by rotating the curve generated by the above equations, about a line which passes through the initial radius $R_0$, to form the surface.

The power increase, or "add" $P_x$ at any point may be defined by the equation:

$$P_x = P_0 + (X*P)/V$$

where:

$P_0$=the power at $R_0$; and

X=the distance from $P_0$ to $P_x$.

As the radius of curvature of the varifocal portion of the lens decreases, the center of curvature for each radii shifts. The locus of the center of curvature of the changing radii follows an arcuate path, and is approximated by the equation:

$$S_x \approx V(1 - R_x/R_0).$$

A pantograph 44, which is an apparatus for transferring three-dimensional tracer pin motions to a cutting tool is illustrated in FIG. 16. The cutting tool 46 moves in the same direction as the tracer pin 48, at a preset, duplicating ratio. The pantograph 44 is employed to replicate the contours of the pattern 28 onto a workpiece 50 which is, in the preferred embodiment, ten times smaller than that of the pattern itself. The pattern 28 and the workpiece 50 are clamped in conjugate positions at roughly the same level to ensure alignment of the cutter 46 and the tracer pin 48. Preferably, the cutter 46 is a high grade tungsten carbide tool, and spins at approximately 20,000 rpm. If the diameters of the tracer pin 48 and the cutter 46 are selected in accordance with the duplicating ratio, and if the points of the tracer pin and cutter are in alignment with the axis of the horizontal pivot shaft (not shown), the cutter 46 will replicate all of the pattern contours onto the workpiece 50 at the designated ratio. The pattern surface is replicated by carefully drawing the tracer pin 48 across the surface of the pattern 50 in small, circular strokes in steps of approximately 0.010". It is noteworthy that reproduction of the pattern 50 at one-tenth the desired size is advantageous in that any slight errors on the surface of the pattern will be proportionally reduced to the scale reduction out on the replica 54, to acceptable tolerances. The tracer pin 48 may be driven manually or by a CNC machine (not shown).

The replica 54 is to be used as a coining mandrel for coining optical surfaces. It is to be understood that the term coining is used to define the permanent deformation of a soft material, as impressed by a harder material. Preferably, the replica, or coining mandrel 54, is a small, cylindrical piece of high-grade, hardenable alloy tool steel, capable of reaching a hardness of 58 Rockwell, Scale C ($R_c$). Most preferably, D-2 steel is used. Once the coining mandrel 54 has been etched with a scaled-down reproduction of the pattern 50, the rough edges developed during the replication process are polished off. Significantly, the peripheral edge 55 of the coining mandrel 54 (FIGS. 17 and 19) is radiused such that when an optical mold is coined, the convexity of the resultant mold cavity will yield a smoothly radiused product. Thus, when two coined mold halves are brought together to form a biconvex lens, the resultant lens will exhibit an ogive shape with a blended, radiused edge, eliminating squared corners typical of traditionally molded intraocular lenses. Further, lenses made in a coined mold cavity will exhibit only one flash line which can be easily abraded away using standard tumbling techniques, whereas the squared corners of a traditionally molded lens cannot be tumbled to produce an ogive shaped intraocular lens.

The coining mandrel 54 is then heat treated in an oven to harden the D-2 steel throughout to a hardness of between 58 to 62 Rockwell, Scale C ($R_c$), and most preferably, 60 $R_c$ which corresponds to a tensile strength of 320,000 p.s.i. Because oxygen tends to leave an undesirable coating on the surface of the steel during the heat treating process which would have to be sand-blasted off, the coining mandrel 54 is preferably hardened in one of two ways. The preferred way is to evacuate the air out of the oven to produce a vacuum environment and heat the coining mandrel by radiation to approximately 1300°. The coining mandrel is then allowed to slowly cool and will emerge from the oven within the desired range of hardness. As the steel is heated and cooled, its grain structure changes in a predictable manner. Another way of heat treating the coining mandrel to a hardness of between 58 and 62 $R_c$ is to heat it in a Nitrogen oven. This process is much slower than the vacuum method, as the coining mandrel is heated primarily by convection rather than by radiation.

During the heat treating process, the hardness, strength and wear resistance of the coining mandrel are increased, however nicks, scratches and impurities in the steel are also magnified. Thus, once the coining mandrel 54 has been heat treated and hardened to 60 $R_c$, the reverse mold surface 56 must be polished to an optical surface. The general practice is to polish the surface 56 of the mandrel 54 with a succession of polishing agents, progressing from a coarse grit to a finer grit. Because of the nature and intended use of the coining mandrel, as well as the minute surface area of the reverse mold surface, the coining mandrel must be hand polished under a microscope, allowing a better polish.

Polishing the surface 56 of the coining mandrel 54 is a very tedious process, and requires hours of meticulous work. The first step in the optical polishing of the coining mandrel is to remove all of the crowns and crests from the surface which were magnified during the hardening process. This is accomplished by applying a small amount of fine machine oil and 600 grit silicone carbide material to the surface of the coining mandrel and polishing it with small, circular motions using the end of a brass rod followed by the use of 1000 grit silicone carbide. To ensure that the surface of the coining mandrel is not being over polished and that the precisely calculated radii of curvature are maintained, a comparator is used during each step. Once the crowns and crests have been polished off the surface of the coining mandrel, machine oil and aluminum oxide ($Al_2O_3$), having a grit size of one micron (1 m), is employed as a polishing agent, and the surface 56 of the coining mandrel 54 is further hand polished with wood sticks in small circular motions. Next, using a dremmel, or a hand held drill, having a hardened felt surface, the coining mandrel is optically lapped using 0.3 m $Al_2O_3$ and fine machine oil. Finally, the coining mandrel is tumbled in a standard tumbler, as commonly used in the field to tumble and polish intraocular lenses. The tumbler is filled with 1 and 2 mm glass beads, fine machine oil of the type used during the above polishing steps, an anti-settling agent and mineral spirits. Preferably, the anti-settling agent is fumed silicone dioxide, having a particle size of between 0.7 to 2.7 angstroms (Å), as made commercially available under the name Cab-O-Sil fumed silica. The fumed silica is used as a suspending or anti-settling agent in the tumbler and accelerates the polishing process during tumbling. In addition, it is noteworthy that tumbling media such as water or alcohol are not suitable for use in the tumbler when polishing the coining mandrel 54 as these agents would cause electrolysis, which, in turn, would etch the surface 56 of the coining mandrel. Upon cessation of the tumbling process, the coining mandrel should emerge having a highly polished optical surface of the desired configuration.

FIG. 17 illustrates a hardened, polished coining mandrel 54 which is to be used to stamp it's impression into a blank of a softer material, preferably having an optical finish on the face thereof, so as to form an optical power surface within a concave mold cavity. An optical power surface is one which is contoured to focus light rays so that they converge or diverge to form an image. As the coining mandrel has been hardened to 60 $R_c$, the choice of softer materials would appear endless. As illustrated in the partial cross-sectional assembly of FIG. 40, for example, the coining mandrel 54 could be pressed into a polished piece of sheet metal 57, having a resilient backing 59, such as die rubber, placed thereunder. When coining a mold cavity into such a soft material, the coining mandrel 54 need not be hardened to 60 $R_c$, but can be as soft as 40 $R_c$. As the mandrel 54 is pressed into the sheet metal 57, the sheet metal permanently deforms to assume a reverse configuration of the surface 56 of the coining mandrel 54. The rubber backing 59 will yield to the deformation of the sheet metal 57 during the coining process, however will spring back after the coining is completed and the assembly disassembled. It is noteworthy that a minimal amount of pressure is required to create a mold cavity in the sheet metal 57 due to the resilient nature of the rubber backing 59, and the thinness of the sheet metal 57 itself. Molds formed in this manner have the advantage of being light and inexpensive, however, the longevity and number of uses of such a mold is severely limited. Accordingly, in the interest of making a long lasting mold, any grade of good quality stainless steel should be used. Preferably, the blank 58 (shown in FIGS. 18 and 19) is formed of either a 300 type series or a 400 type series stainless steel. Presently, the 300 series is preferred, with 203 or 303 stainless steel proving well suited.

The blank 58 is machined in the desired shape and thickness, and the face 60 is optically lapped in a manner as is well known in the art. Preferably, the face 60 of the blank is polished in a series of steps, beginning with 320 grit sandpaper and oil, and proceeding to finer grades of sandpaper, having grit sizes of 400 and 600. The blank is then polished using a lapping plate, having a urethane cover using 1 m $Al_2O_3$ and water. Finally, the face 60 of the blank 58 is optically finished with a rotary polisher, having a urethane felt cover, in a 0.3 m $Al_2O_3$ and water slurry.

Following the optical polishing of the face of the blank, a mold cavity is ready to be formed. As shown in FIGS. 18 and 19, a pair of drill bushings 62, 64, are utilized to maintain the relative positioning of the coining mandrel 54 with respect to the diametric center of the polished blank 58. Preferably, the bushings are formed of tool steel, as they will ultimately be subjected to exceptionally high loads. The outer bushing 62 is cored and has an inner diameter 66 sized to receive and center the polished blank 58 with minimal clearance about the periphery thereof, so as to ensure that the blank will not move during the mold formation process. Similarly, the inner bushing 64 is also cored, having an outer diameter 68 selected such that the inner bushing 64 will be centered with respect to the outer bushing 62 and an inner diameter 70, for centering the coining mandrel 54 will be centered with respect to the blank 58. The inner bushing 64 is further equipped with a flange 72, adapted to rest on the upper rim 74 of the outer bushing 62 to maintain a small gap 76 between the bottom surface 78 of the inner bushing 64 and the blank 58.

To form a mold cavity, the outer bushing 62 is placed on a hardened surface 80. The blank 58 is inserted into the core 66 of the outer drill bushing 62, with the polished side up. It is important to execute care in the insertion of the blank 58 into the bushing 62, as scratches on the surface 60 of the blank 58 may result in a mold cavity which yields flawed lenses. The inner bushing 64 is then inserted into the core 66 of the outer bushing 62, so that the flange 72 rests on the upper rim 74 of the outer drill bushing 62 and finally, the coining mandrel 54 is lowered into the core 70 of the inner bushing 64 until it just touches the surface 60 of the blank 58. A second hardened surface 82 is carefully set on top of the coining mandrel 54, and the formation assembly 84 is put into a hydraulic press (not shown).

It is noteworthy that the coining mandrel 54 should extend outwardly above the flange 72 of the inner bushing 64, by an amount equal to the desired final depth of the mold cavity, taking into account the amount of compression, or shrinkage of the coining mandrel expected during the pressing of the mold cavity. Preferably, the coining mandrel 54 extends 0.043 inches above the flanged surface 72, allowing 0.012 inches for compression of the coining mandrel under full load, and will yield an imprint having a final depth of 0.031 inches. Because the 0.043 inch gap 88 is directly related to the desired depth of the resultant mold cavity, the hydraulic press may be slowly and steadily loaded until the gap 88 disappears. In general, it takes a load of between 7 and 10 tons to stamp the coining mandrel impression into the steel blank at the desired depth. Preferably, the hydraulic press is loaded to 10 tons to ensure proper deformation of the mold cavity. A load of this magnitude imposes a pressure in excess of 400,000 p.s.i. upon the surface 56 of the coining mandrel 54. In order to allow for the creeping of the materials, the press remains under full load for approximately 15 minutes after the gap 88 disappears.

As mentioned above, upon application of full load, the coining mandrel 54 compresses 0.012 inches. In addition, a radial expansion of approximately 0.001 inches in diameter is also experienced. However, the coining mandrel is not deformed beyond the elastic limit of the material, and therefore returns to its original form upon removal of the load. Unlike the coining mandrel 54, the stainless steel blank 58 has a much lower yield strength and therefore undergoes permanent deformation upon application of the load. Thus, not only does the newly formed mold half 90 exhibit a mold cavity 92, having a reverse imprint of the surface 56 of the coining mandrel 54 at the desired depth, as shown in FIG. 20, but also undergoes a radial expansion, resulting in an interference fit within the core 66 of the outer bushing 62 as well as a slight eruption 94 (FIG. 21) about the periphery of the mold cavity 92. After the load has been removed, the coining mandrel 54 and the inner bushing 64 are lifted from the formation assembly 84. The pressed mold half 90, however, must be forced out of the outer bushing 62 due to the interference fit caused by the radial expansion of the mold half 90. Significantly, during the mold forming process, slight imperfections present on the surface 60 of the blank 58 in the localized area of the mold cavity 92 are ironed out. Further, due to the tremendous force applied to the materials, the porosity in the mold cavity 92 is substantially decreased, resulting in a smoother, higher quality optical surface than was present on the original optically polished blank, and the deformation of the blank material work hardens, resulting in a harder, more durable surface.

Figure 26:
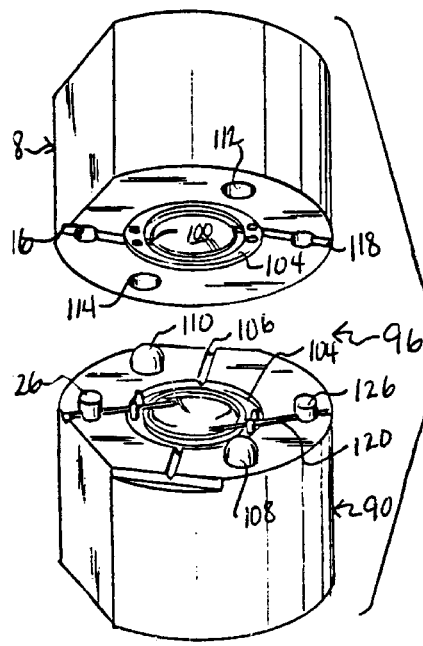
FIG. 26 is a perspective view of the mold halves situated one over the other prior to the formation of a lens.

As shown in FIG. 26, the mold 96 used to form the biconvex intraocular lens 10 of the present invention comprises an upper mold half 98 with an upper concave cavity 100 and a lower mold half 90 with a lower concave cavity 92. Thus, in order to complete the mold 96 for a biconvex lens 10, a second, or upper mold half 98 must be made. Preferably, the mold cavity 100 of the upper mold half 98 will have a spherical surface which will provide the desired additional base power of the lens. The upper mold half 98 is made in the same manner as the lower mold half 90 with the exception of the surface configuration of the mold cavity. The upper mold cavity 100 is preferably spherical, having a radius of curvature selected in accordance with the desired refractive power of the resultant lens. Having formed the concave cavities 92, 100 in each of the mold halves 90, 98, the eruptions 94 (FIG. 21) surrounding the periphery of each cavity must be ground off. Advantageously, each mold cavity 92, 100 was pressed in to a depth of 0.031 inches to allow for imperfections in the blank 58, as well as these eruptions 94. To protect the optical surface of the mold cavities 92, 100 during subsequent processing, an adhesive backed disc 193, or other type of covering, having a light adhesive backing to prevent slippage and having a known thickness, is carefully placed on the surface of each mold cavity during the grinding and machining processes. As shown in FIG. 22, the face 102 of each mold half 90, 98 is ground down until a final mold cavity depth of 0.025 inches is attained.

Figure 24:
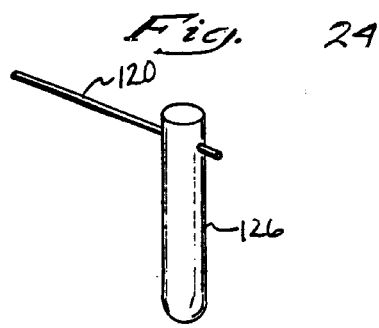
FIG. 24 is a perspective view of a core pin and post assembly.
Figure 25:
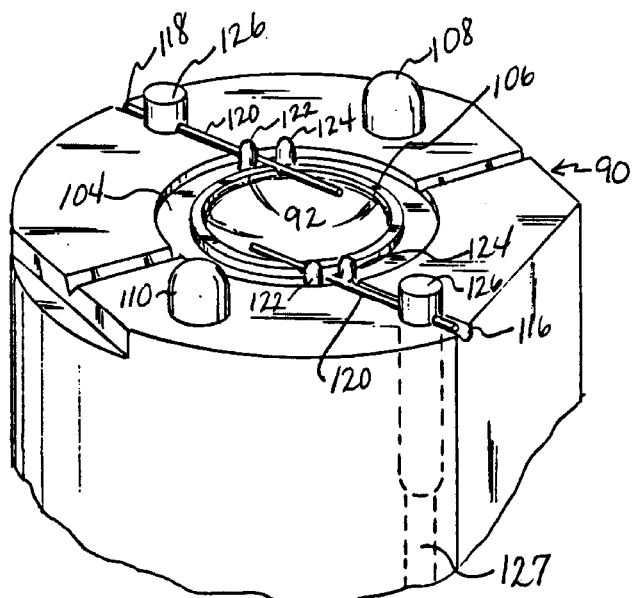
FIG. 25 is a perspective view of a bottom half of a mold, showing the insertion of the core pin and post assembly of FIG. 24 in dashed lines.

With the adhesive backed disc 193 still in place, an overflow groove 104 is machined using a lathe, around the periphery of each mold cavity 92, 100. A thin ridge 106, referred to as the mold shut off, or flash line, is created intermediate the groove 104 and the respective mold cavity 92, 100 so that concentric circles are formed about the mold cavity. The flash line 106 defines the outer limits of the molded lens. As illustrated in FIG. 25, in order to ensure proper alignment of the mold halves 90, 98 during the molding process, a pair of alignment dowel pins 108, 110, are secured to the bottom half of the mold 90 in a conventional manner. Associated mating holes 112, 114 are drilled into the top half of the mold 98 (FIG. 23) to receive and retain the dowel pins 108, 110 during the molding process. Each mold half 90, 98 is machined to provide a pair of elongate grooves 116, 118 on diametrically opposed sides of the mold. The elongate grooves 116, 118 are semi-cylindrical in cross-section and are adapted to receive and maintain the positioning of a pair of core pins 120, about which the silicone lens material will cure during its production. To further ensure the stability of the core pins within the mold cavity during the production of the lens, a pair of small dowel pins 122, 124 is provided in the overflow groove 104, on opposite sides of each core pin 120, to sandwich the core pin therebetween. Advantageously, as illustrated in FIGS. 24 and 25, each core pin 120 is secured to a post 126, which is removable from the bottom mold half 90. Thus, after the lens is formed, the core pins 120 may be lifted from the mold, together with the lens so that the core pins do not tear the lens during the removal of the lens from the mold. In actual practice, the lens is removed from the mold by pushing the posts 126 upwardly from the bottom half of the mold 90 through the hole 127 with a lifter pin (not shown). In this manner, the optical power surfaces of the mold are less likely to be damaged by removing tools being inserted under the lens.

FIG. 26 illustrates a complete mold assembly 96. The upper and lower halves of the mold 90, 98 are relatively movable towards and away from each other to allow the introduction of material which will form the optical element therein. Preferably, the lenses are produced via compression molding, although other molding processes, such as injection molding, may also be employed. Silicone, in a liquid form, having a volume somewhat greater than that of the two mold cavities is introduced into the lower mold cavity 99. Preferably, about 0.025 milliliters of uncured, liquid silicone is used to form the lens. The upper half of the mold 98 is then brought into engagement with the lower half 92 so that the alignment dowel pins 108, 110 are met by the associated mating holes 112, 114. Once the mold 96 is closed, the excess volume of silicone will leak out between the mold parts and into the overflow grooves 104. The mold 96 is then heated for a predetermined time at an elevated predetermined temperature that will polymerize the monomers located therein into a solid polymer. In the preferred embodiment, the mold is heated for 10 minutes at 300° F. Following the polymerization of the optical element material, the mold is opened, and the optical element is removed therefrom.

As mentioned above, the core pins 120 are lifted from the mold along with the optical element. The core pins are then carefully removed by slowly twisting and then withdrawing the them in a plane parallel to the lens. As illustrated in FIGS. 27 and 28, the resultant lens 128 includes a pair of diametrically opposed apertures 130, 132 corresponding to the area from which the core pins 120 were removed. In addition, a small amount of flash 134, created during the production of the lens at the flash line 106 will be sporadically disposed about the edge 136 of the lens 128. Significantly, there is only one flash line 106 on the just-formed lens 128, and the edge 136 is ogive in shape. The lens 128 is then tumbled to remove the flash 134 from the periphery of the lens and to polish the edges thereof.

Preferably, the tumbler is filled with 1 to 6 mm glass beads, isopropyl alcohol, and fumed silicone dioxide. Typically, $Al_2O_3$ is used as the polishing agent when tumbling PMMA lenses to speed up the tumbling process and water is used as the tumbling medium. Undesirably, however, $Al_2O_3$ tends to leave a residue on silicone lenses and therefore, fumed silicone dioxide is used as the polishing agent to accelerate the tumbling process. When using fumed silicone dioxide as a polishing agent and water, the silicone lenses tend to float out and not polish. Isopropyl alcohol, however, has a lower surface tension than water, and a lower specific gravity than silicone and will allow the lenses to sink, thereby making it an ideal tumbling matrix. The isopropyl alcohol has another advantage in that the silicone lens material absorbs a portion of the alcohol, causing the lenses to uniformly swell an average of 7%, which in turn, lowers the tear strength of the lens material. As the tear strength decreases, the abrading process, caused by the tumbling action of the tumbler, is further accelerated.

The tumbling process tends to abrade more rapidly at lip or margin 138 of the holes 130, 132 formed by the core pins during the production of the lens because this area of the lens is thinner. This is significant in that, as illustrated in FIG. 29, at the cessation of the tumbling process, the optical element 140 is left with an indentation 142 proximate the holes 130, 132. Further, the flash, created during the production of the lens in the area where the two mold halves met, substantially disappears after tumbling, leaving a smoothly radiused, ogive shaped lens having a blended, radiused edge. In addition, a thin layer of fumed silicone dioxide will be present on both the outer surface of the lens, as well as the surface within the holes 130, 132. It has been found that this residue improves subsequent adhesive bonding of the haptics 22, 24 within the holes 130, 132 and is therefore left on the inner surface thereof. The fumed silicone dioxide residue on the outer surface of the lens, however, will be rinsed off, using standard cleaning and extraction techniques.

FIGS. 30–32 illustrate a forming mandrel 144 for making control haptics 22. Haptics 22, 24 may be formed from any material, but are preferably formed from a solid polymer member, designed to be relatively thin and flexible, yet provide sufficient support for the optical element 140. Materials found well suited to the formation of haptics include polypropylene, PMMA, polyamide, polyethylene, nylon, and great number of extruded plastics. Preferably, the haptics are formed of polypropylene, or any 5-0 medical non-abradable suture, having a substantially circular cross-section of approximately 0.006 inches in diameter, as commonly available from Ethicon, a division of Johnson and Johnson, as well as Davis and Geck, a division of American Cyanamide. The forming mandrel 144 comprises a base 146 upon which a pair of forming blocks 148, 150 are mounted. Block 148 is adapted to form the distal, or free end 152 of the haptic while block 150 is precisely formed to the desired contours of the proximal end 154 of the haptic. The blocks 148, 150 are positioned on the base 146, adjacent one another, leaving a small void 156 therebetween.

A control loop pin 158, sized slightly larger than the void 156, is provided for the formation of the horseshoe-like kink 26, characteristic of the control haptic 22. The control loop pin 158 is sized such that when the suture material is wrapped around it, as illustrated in FIGS. 30–32, the combination of the control loop pin 158 and the suture material is larger than the void 156. This is significant in that it will yield a control haptic 22, having a control loop 26 with a kinked portion which is greater than 180°, but less than 360°, to assist the ophthalmic surgeon in more readily determining which is the superior side of the lens. More simply stated, the kinked portion of the control loop 26 is at least semi-circular, having an eyelet-like shape, but does not form a complete circle. As illustrated more clearly in FIGS. 31 and 32, the control loop pin 158 is placed between the blocks 148, 150 and both ends of the suture are passed through the void 156. The suture 160 is then pulled tightly against the blocks 148, 150, conforming to the contours of the forming mandrel 144, and secured thereto, preferably by tying a knot in the suture material, intermediate blocks 148, 150 and opposite the control loop pin 158. A retaining bar (not shown) is placed against the control loop pin 158 intermediate the blocks 148, 150 to bias the suture material 160 toward the pin during the remainder of the control haptic forming process. The wrapped forming mandrel is then placed in a Nitrogen oven and heated at a temperature of between 300° F. and 350° F. for approximately one hour. Preferably, the suture material is heat set at 320° F., during which time it will deform to assume the shape of the forming mandrel 144, and produce a control haptic 22. After the mandrel and haptics have been allowed to cool, they are cut off of the forming mandrel with a razor blade along grooves 162 and 164. Haptics without the control loop may also be formed by the same procedure, without the use of the control loop pin. The haptics are then tumbled in a standard intraocular lens tumbler, using the standard proportions of water, 0.3 m $Al_2O_3$ and glass beads to round off the ends of the haptics. The resultant control haptic 22 is illustrated in FIG. 33. The proximal end 154 of the haptic is somewhat bent at an angle, so that the haptic, when bonded to the optical element 140, will be tangential thereto. Prior to bonding the haptics 22, 24 within the apertures 130, 132 formed in the lens, they must be surgically cleaned. This is accomplished by thoroughly rinsing the haptics in isopropyl alcohol, heated to about 150° F.

In order to improve the adhesive properties of the polypropylene suture material from which the haptics are made, a high frequency corona surface treater (not shown) is used to surface charge the proximal end 154 of the haptic. Such surface treatment is not permanent, and decays with time to some limiting value which is dependent upon the particular material being used. Further, corona treated surfaces are not mechanically durable, and should therefore be disturbed as little as possible. The proximal end of the haptic, which is to be surface treated by the corona discharge is passed beneath an emitting electrode at a speed and distance from the electrode which is determined by the amount of treatment required.

Because of the sensitivity of the surface treatment, the treated end of the haptic is preferably coated with a primer immediately after being passed through the corona discharge. Preferably, a specially formulated, one component unpigmented silicone primer, as available from McGhan NuSil Corporation, and sold under the name CF1-135 High Technology Silicone Primer, is used. This primer is an air-drying primer, designed to improve the adhesion of cured silicones to various substrates. A uniform thin coat of primer should be applied to the proximal end of the haptic following treatment of the surface. This may be accomplished by brushing, wiping, dipping or spraying the primer onto the haptic, although dipping is the preferred method. The primer is then allowed to hydrolyze, or air-dry on the surface of the haptic, at least two hours prior to bonding. While the adhesion of the primer to the haptic is much improved after the haptic has been subjected to the corona discharge, it is sometimes necessary to dip the proximal end of the haptic in the primer several times before it is uniformly coated. To further improve the adhesion of the haptics 22, 24, within the holes 130, 132, the proximal end of the haptics may be dusted with fumed silicone dioxide after the primer has been allowed to dry.

Following the preparation of the haptics 22, 24 for bonding to the optical element 140, a silicone adhesive 166 is drawn into a 1 cc tuberculin syringe 168, shown in FIG. 34. Preferably, the adhesive is RTV-118 silicone rubber adhesive sealant, as commonly available from the Silicone Products Division of General Electric. Alternatively, the adhesive can be medical adhesive silicone type A, as manufactured by Dow Corning Corporation, under the name Silastic. These adhesives are easily applied, translucent, non-flowing soft silicone adhesives, ideally suited for bonding silicone elastomers to itself as well as other synthetics. A 30 gauge needle 170, having a diameter of 0.012", and a blunt end 172 which has been cut off and polished round, as illustrated in FIG. 34, is secured to the end of the syringe 168. Prior to the injection of the adhesive 166 into the apertures 130, 132, the needle 170 is fully inserted into the aperture. The adhesive 166 is then slowly injected and the syringe slowly withdrawn from the aperture until the aperture is approximately two-thirds full of adhesive. It is important that the syringe needle 170 be fully inserted into the aperture and backed out of the aperture while the adhesive is being injected, as air pressure in the aperture would tend to force the adhesive outward. The proximal end 154 of the haptic is then inserted into the adhesive-filled aperture as illustrated in FIG. 35, displacing a small quantity of the adhesive.

It is beneficial to have as long a haptic as possible without unduly increasing the size of the intraocular lens. Longer haptics have the advantage over shorter haptics in that they are less rigid, substantially softer and more flexible and, most importantly, less traumatic to the eye after implantation. A haptic that completely encircles the optical element of the intraocular lens, however, would not be preferable, as it would increase the surface area of the lens, necessitating a larger incision into the eye for implanting. Fortunately, because of the indentation 142 at the lip 138 of the lens 140 formed during the tumbling process, and the angle at which the proximal end 154 of the haptic is subtended, the haptic emerges tangentially from the lens. The tangential alignment and bonding of the haptic with the lens enables the implementation of a haptic having the maximum possible length without necessitating an increase in width. This is significant in that it allows one to use a longer haptic, having the aforementioned advantages of suppleness and flexibility which are instrumental in providing a comfortable and non-irritating means for fixating and properly positioning the intraocular lens within the eye. In addition, since the width of the intraocular lens is not affected by the increased length of the haptic, the advantage of smaller incisions, made possible by the advances in phacoemulsification technology and associated with soft, foldable intraocular lenses is preserved. Advantageously, as shown in FIG. 36, because the haptic is one half the diameter of the aperture, it may be disposed at any number of desirable angles with respect to the lens.

FIGS. 37 and 38 illustrate a dihedral fixture 174, having a pair of upwardly sloping sides 176, 178 and a pair of opposing sidewalls 180, 182 disposed along the upper edges 184, 186 of the sloping sides. Preferably, the dihedral fixture 174 has an included angle of 172° so as to provide for a 4° inclined surface on each of the sloping sides 176, 178. Centrally disposed between the opposing sidewalls 180, 182 of the fixture are a plurality of depressed receptacles 188, resting in a valley 190 created by the sloping sides 176, 178 of the forming fixture 174. Each receptacle 188 is sized to accommodate one intraocular lens. Small coves 192 are cut into the opposing sidewalls 180, 182 to provide receptacles for the haptics 22, 24 during the time the adhesive 166 is curing. The intraocular lens 10 is carefully placed into the depressed receptacle 188 which, because of its sunken disposition, adds an extra degree to the angulation of the haptic with respect to the lens, resulting in an intraocular lens 10 having haptics 22, 24 set at a 5° angle with respect to the lens.

As a final production step, the lenses 10, with the haptics attached, are extracted, or rinsed in distilled, purified water to remove any residues from the adhesive or impurities which may be present on the lens. The intraocular lenses are further agitated in the purified water for a period of at least 12 hours to draw out such impurities. The lenses are then dried, and the haptic attachment is tested for durability on a gram scale.

It will be understood by those skilled in the art that the coining mandrel of the present invention can assume any desired configuration, and that the mold forming process described herein may be used for intraocular lenses other than biconvex. The foregoing detailed description is to be clearly understood as given by way of illustration, the spirit and scope of this invention limited solely by the appended claims.

What is claimed is:

1. An intraocular implant to replace the crystalline lens of a patient's eye, comprising:
   an intraocular aspheric lens formed of soft, biocompatible material, wherein said material is silicone.

* * * * *